Figure 1:
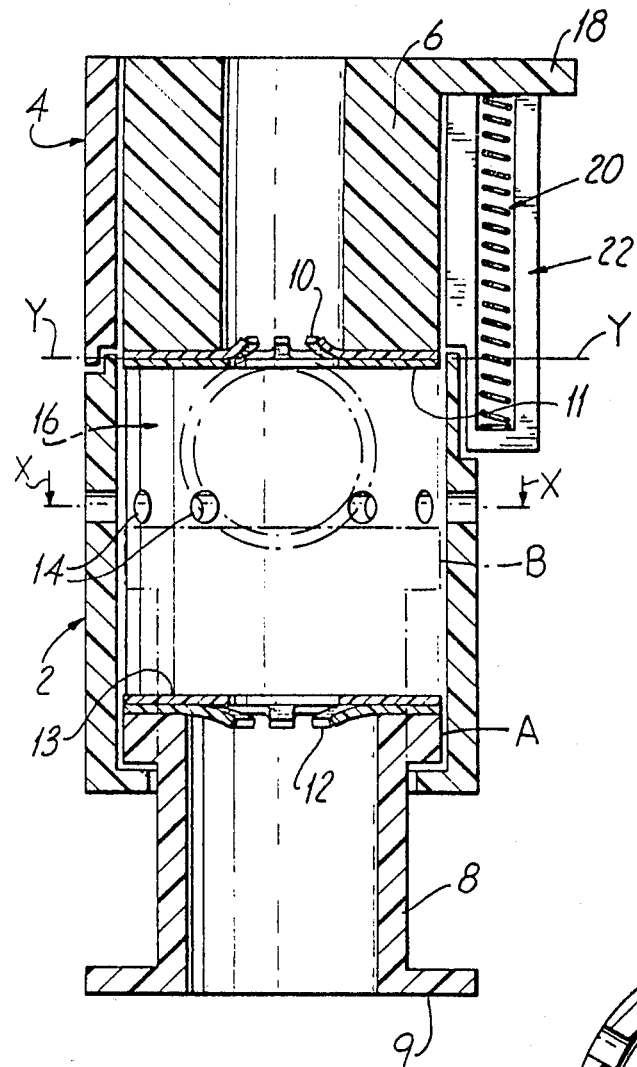

United States Patent [19]

Baum et al.

[11] 4,446,862

[45] May 8, 1984

[54] BREATH ACTUATED DEVICES FOR ADMINISTERING POWDERED MEDICAMENTS

[76] Inventors: Eric A. Baum; Leslie J. Davies, both c/o Minnesota 3M Research Limited, The Pinnacles, Harlow, Essex, England, CM19 5AE; William F. Kirk, 1 Morley St., Loughborough, Leicestershire; Anthony C. L. Wass, The Mousehole, Duddington Stamford, Lincolnshire, both of England

[21] Appl. No.: 279,977

[22] PCT Filed: Oct. 30, 1980

[86] PCT No.: PCT/GB80/00187
§ 371 Date: Jun. 29, 1981
§ 102(e) Date: Jun. 29, 1981

[87] PCT Pub. No.: WO81/01243
PCT Pub. Date: May 14, 1981

[30] Foreign Application Priority Data

Oct. 30, 1979 [GB] United Kingdom ............... 7937519

[51] Int. Cl.³ ............................................. A61M 15/06
[52] U.S. Cl. ............................................. 128/203.15
[58] Field of Search ............... 128/203.15, 266, 203.19, 128/203.18; 222/630

[56] References Cited

U.S. PATENT DOCUMENTS

| | | | |
|---|---|---|---|
| 3,906,950 | 9/1975 | Cocozza | 128/203.15 |
| 4,116,195 | 9/1978 | James | 128/203.15 |
| 4,192,309 | 3/1980 | Poulsen | 128/203.15 |
| 4,206,758 | 6/1980 | Hallworth et al. | 128/203.15 |
| 4,210,140 | 7/1980 | James et al. | 128/266 |

FOREIGN PATENT DOCUMENTS 2804852 10/1977 Fed. Rep. of Germany ............... 128/203.15
1520064 8/1978 United Kingdom .

Primary Examiner—Benjamin R. Padgett
Assistant Examiner—T. J. Wallen
Attorney, Agent, or Firm—Donald M. Sell; James A. Smith; William L. Huebsch

[57] ABSTRACT

A breath actuated device for the oral inhalation of medicaments in finely divided powder form, comprising a chamber (72) having one or more inlet ports for the entry of air and an outlet in direct communication with a mouthpiece (66) and positioned within the chamber, means for separating the lid and base components (62A, 62B) of a capsule (as defined herein) containing the medicament while holding the capsule substantially vertically to expose an aperture in the base component facilitating access to the powdered medicament and means for supporting the base component of the capsule containing the powdered medicament in a substantially vertical position, the inlet ports, outlet port and means for supporting the base component of the capsule being arranged such that when the device is operated by suction at the mouthpiece an air flow is established from the entry ports to the outlet port directly across the aperture in the base component of the capsule causing the particles of powdered medicament in the base component of the capsule to become entrained in the air flow.

In a preferred embodiment the device comprises a carousel (54) which retains a plurality of capsules (62) and may be rotated to introduce the capsules sequentially into the chamber (72). The means for separating the two components of the capsule may comprise a piston assembly (58) movable between an engaging position in which the piston grips the lid of the capsule (62A) and a dispensing position, said movement causing the lid of the capsule to be removed from the base (62B).

13 Claims, 15 Drawing Figures

BREATH ACTUATED DEVICES FOR ADMINISTERING POWDERED MEDICAMENTS

This invention relates to a device for administering powdered medicaments by oral inhalation and which is actuated by the inhalation of the patient.

There are many devices for administering powdered medicaments to the alveolar region of the lungs which employ propellants, such as compressed gases, e.g. air, or liquefied gas propellants, to dispense and disperse the medicament. These devices tend to be complex to construct and have the disadvantage that in order for the optimum effect to be obtained it is essential that inhalation and dispensing be synchronous.

There are also a number of known breath actuated inhalation devices for administering powdered medicaments to the lungs which have mouthpieces through which the medicament is inhaled. The powdered medicament is usually supplied in capsules which are substantially cylindrical in shape and have rounded ends. The capsule is formed in two halves having different diameters, one half being a push-fit within the other. In the simpler breath actuated devices the capsule is opened prior to insertion into the device and one half of the capsule containing the medicament or the medicament itself is positioned in the device such that during inhalation through the mouthpiece the medicament becomes entrained in the air stream and passes to the patient. Examples of such devices are disclosed in British Patent Specification Nos. 1 520 064, 1 504 441, 1 118 341, 1 520 063 and 1 520 062. These devices suffer from the disadvantage that medicament may be spilled when the capsule is opened prior to insertion in the device.

British Patent Specification Nos. 1 521 000, 1 520 062, 1 472 650 and 1 502 150 disclose more complex devices in which the complete capsule is inserted into the device thus ensuring no spillage of medicament prior to inhalation, and access to the medicament is gained by piercing the capsule or cutting it in half, inside the dispensing device. On inhalation the air flows into or through the capsule and the powder within is released into the air stream and flows towards the mouth.

The devices disclosed in British Patent Specification Nos. 1 485 163, 1 331 216, 1 457 352, 1 396 258, 1 182 779, 1 404 338, 1 459 426 and 1 118 431 and U.S. Patent Specification Nos. 4 117 844 and 4 116 195 are designed to agitate the capsule containing the medicament in order to help release and disperse the powder from the capsule. The capsule may be agitated by various means, e.g. creating a turbulent air flow, or by rotational and/or vibrational motion of the capsule with the use of vanes or propellors. These devices incorporate complex arrangements and are often difficult to operate.

U.S. Patent Specification No. 4 210 140 discloses a device in which access to the powdered medicament is gained by pulling the halves of the capsule apart so that the medicament is emptied to a suitable position for entrainment in the air flow caused by inhalation.

In spite of the numerous prior art devices there is a need for a breath actuated device which is simple to operate and efficient in administering powdered medicaments into the alveolar region of the lungs.

The present invention provides a breath actuated device for the oral inhalation of medicaments in finely divided powder form, comprising a chamber having one or more inlet ports for the entry of air and an outlet in direct communication with a mouthpiece and, positioned within the chamber, means for separating the lid and base components of a capsule (as defined herein) containing the medicament whilst holding the capsule substantially vertically to expose an aperture in the base component facilitating access to the powdered medicament and means for supporting the base component of the capsule containing the powdered medicament in a substantially vertical position, the inlet ports, outlet port and means for supporting the base component of the capsule being arranged such that when the device is operated by suction at the mouthpiece an air flow is established from the inlet ports to the outlet port directly across the aperture in the base component of the capsule causing the particles of powdered medicament in the base component of the capsule to become entrained in the air flow.

The invention also provides a breath actuated device for oral inhalation of medicament in finely divided powder form, comprising a chamber having one or more inlet ports for entry of air and an outlet port in direct communication with a mouthpiece and, positioned within the chamber, the base component of a capsule (as defined herein) containing said medicament, the base component of the capsule being mounted substantially vertically and having a substantially horizontal rim defining an aperture, the inlet ports and outlet port being arranged such that when the device is operated by suction at the mouthpiece an air flow is established from the inlet ports to the outlet port directly across and substantially parallel to said rim causing particles of medicament to become entrained in said air flow.

The term "capsule" used herein refers to an enclosed container suitable for powdered medicament formed from a base component and a lid component, the base component being capable of holding powdered medicament and the lid component being capable of being removed to expose the powdered medicament in the base component.

In the operation of the devices of the invention it is the base component of the capsule which contains the powdered medicament, the lid component having been removed.

Whilst the invention is described mainly with reference to conventional capsules used in the pharmaceutical industry which are substantially cylindrical and are formed of two halves, one being a force fit within the other, the invention is equally applicable to other containers in which accesss to the contents is gained by removal of a lid component, e.g. a tube having a bung or a container having a foil lid adhered or crimped over the open end. The devices of the invention may include the base component of the capsule integrally mounted therein as will be described hereinafter.

The device according to the invention is simple to operate and is effective in transferring medicaments to the lungs. The complete capsule containing medicament is placed in the device thereby preventing spillage of the medicament and the lid and base components of the capsules are separated, e.g. by pulling apart within the device to allow direct and efficient access to the powder held in the base component without need for the operator to manually handle the capsule during the opening operation. A mouthpiece is arranged with direct access to the chamber in which the base component of the capsule containing the medicament is held in order that the medicament may have a short direct path to the mouth. Constructions, corners or obstructions would hinder the passage of powder. The inlet port or ports to the chamber, which may be in the form of a slit or a plurality of radial apertures, are arranged to provide an air flow passing directly over the aperture in the base of the capsule containing medicament so that the powder contained in the capsule base component will be entrained into the air stream.

The airflow established in the device of the invention is directed uniformly across the open aperture and not into the base component of the capsule. This airflow is effective in entraining powder from the capsule possibly due to a resonance effect built up in the capsule (in a similar manner to blowing over the top of an open bottle). Tests which have been conducted reveal that for optimum efficiency the airflow must be across the open aperture and there tends to be an optimum position for the medicament and hence the capsule relative to the lower extent of the inlet ports, i.e. relative to the airflow. This optimum position may vary according to capsule dimensions and the amount of medicament in the capsule but does not tend to be critical for capsule bases which are relatively shallow, e.g. up to 10 mm, but becomes more critical when deeper capsule bases are used. In general it has been found that the rim of the capsule should not extend significantly above the lower extent of the inlet ports and is preferably at the same level or slightly lower than the lower extent of the inlet ports, i.e. the medicament in the capsule base is spaced slightly from the mainstream of the airflow. Preferably, the device of the invention is arranged to take a particular size of base component of a capsule and includes means to accurately position the capsule base in the optimum position for powder entrainment in the airflow.

The efficiency achieved by using an airflow directly across the aperture of the base of the capsule is surprising since heretofore it was always believed that the airflow in such devices should impinge directly onto the powder and devices of the prior art were specifically designed to create sufficient turbulence in order to entrain the powder in the airflow. For example, the device disclosed in U.S. Patent Sepcification No. 4 192 309 which utilizes a vertically positioned opened capsule as a powder reservoir deliberately incorporates a deflector to deflect the air steam into the opened capsule to entrain the powder. Tests conducted on the device in accordance with the invention have shown that the inclusion of a deflector to deflect air into the caspule does not affect the efficiency of the device.

The inlet and outlet ports of the chamber are arranged so that the airflow from the former to the latter passes directly over the opened capsule base. The lower extent of the inlet port is preferably at the same height or higher than the lower extent of the outlet port and the vertical extent of the aperture of the inlet ports is wholly within that of the outlet port so that in use a substantially horizontal flow of air passes from inlet to outlet across the opened capsule base. The total cross-sectional area of the inlet ports is small compared with that of the outlet port so that the velocity of the air across the capsule base is high. However, the pressure drop across the chamber in use should not be high since this would require the user to exert considerable suction at a time when he is in a distressed condition. In practice it has been found that it is possible to achieve a suitable arrangement of inlet and outlet ports which will give the desired airflow and will cause a pressure drop of about 5 cm of water which is barely noticeable to the user. A pressure drop of up to 25 cm of water appears to be an upper limit as far as comfort to the user is concerned.

The mouthpiece is preferably short and straight and aligned with the airflow across the chamber so that there is a substantially straight airflow across the device. However, the mouthpiece may be shaped or inclined slightly with respect to the airflow across the chamber without significantly affecting the efficiency of the device providing there are no obstructions which will trap the particles entrained in the airflow. The mouthpiece of the device may be adapted for nasal inhalation and the term "mouthpiece" used herein includes such nasal adaptors.

According to one embodiment the capsule base component containing the medicament is supported vertically on a sliding piston arrangement so that when the device is operated by suction the piston is urged upwards by reduced pressure until it abuts a stop; this action gives the powder an initial impetus which aids in the dispersion of the powder as the air stream flows across the open end of the capsule. This embodiment is particularly effective when the powder in the capsule has become compacted although the piston arrangement is not necessary for free flowing powders.

The means for separating the two components of the capsule may comprise an opening means movable between an engaging position in which the opening means engages the lid component of a capsule held by the base component in the securing means, and a dispensing position whereby movement of the opening means for its engaging position to its dispensing position causes separation of the two components of the capsule.

According to one embodiment of the invention the chamber is substantially cylindrical in shape and the device is hinged to give access to the chamber for insertion of the capsule. The roof of the chamber is provided with a clutch into which the capsule is inserted, the clutch gripping the lid component of the capsule. The base of the chamber is similarly provided with a clutch mechanism and by relative movement of the roof and the base of the chamber towards each other, the base component of the capsule may be engaged in the clutch at the base. Relative movement of the roof and the base of the chamber away from each other separates the two components of the capsule, the base component of the capsule holding the medicament being supported vertically by the clutch of the base. The mouthpiece is provided in one side of the chamber and a number of radial inlet ports are provided which are coplanar and are disposed over not more than 180°. The axis of the mouthpiece preferably bisects the angular spread of the inlet ports, the lower extent of the inlet ports being higher than the lower extent of the outlet port, the vertical extent of the inlet ports being wholly within that of the outlet port. The top of the base component of the capsule is arranged at substantially the same height or below the lower extent of the inlet ports. The base of the chamber may be a movable piston arrangement as described above.

The invention also provides a device including a conveyor containing a plurality of capsules which may be introduced into the chamber in turn, opened and the medicament dispensed thereby allowing several doses to be sequentially inhaled without recharging the device. In a preferred embodiment the device comprises a carousel which retains a plurality of capsules by their base components (or includes the base components integrally moulded therein) and may be rotated to introduce the capsules sequentially into the chamber. The carousel may be moulded from plastics material and may include partitions or ribs to define one or more walls and the floor of the chamber around each capsule.

The device may include a body portion having the mouthpiece integral therewith, the body containing and supporting a carousel. A lid may be provided hinged to the body, the lid covering the top of the carousel, the opening means and the mouthpiece. In a preferred embodiment the device is constructed so that when the lid is closed the opening means is in the engaging position and when the lid is raised the opening means moves to its dispensing position thereby opening the capsule in the chamber. This is particularly desirable when the device is used by asthmatic patients since the operations required by the patient to gain relief during an asthmatic attack are minimal, the lid of the device is simply raised and the medicament inhaled.

Figure 2:
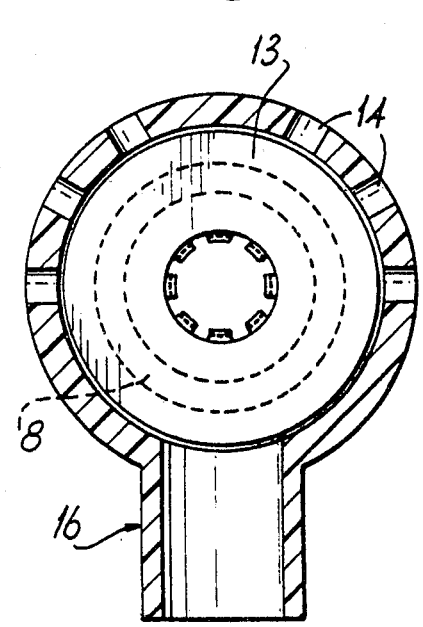
Figure 3:
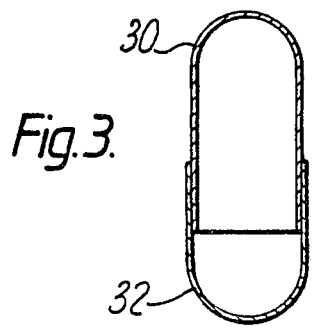
Figure 4:
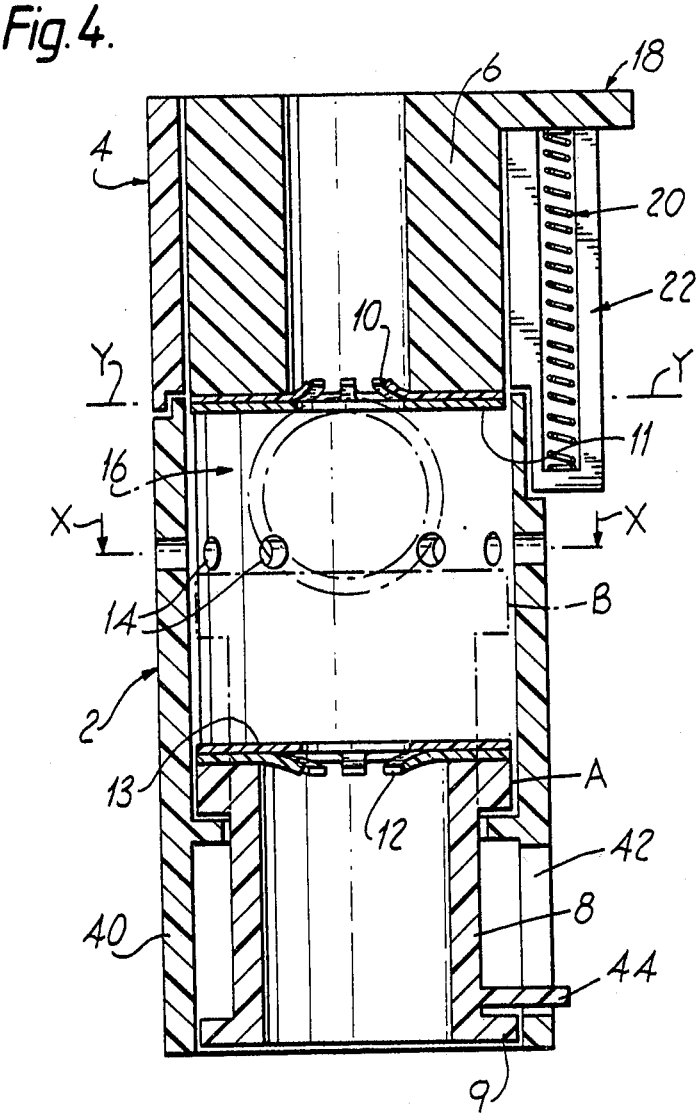
Figure 4A:
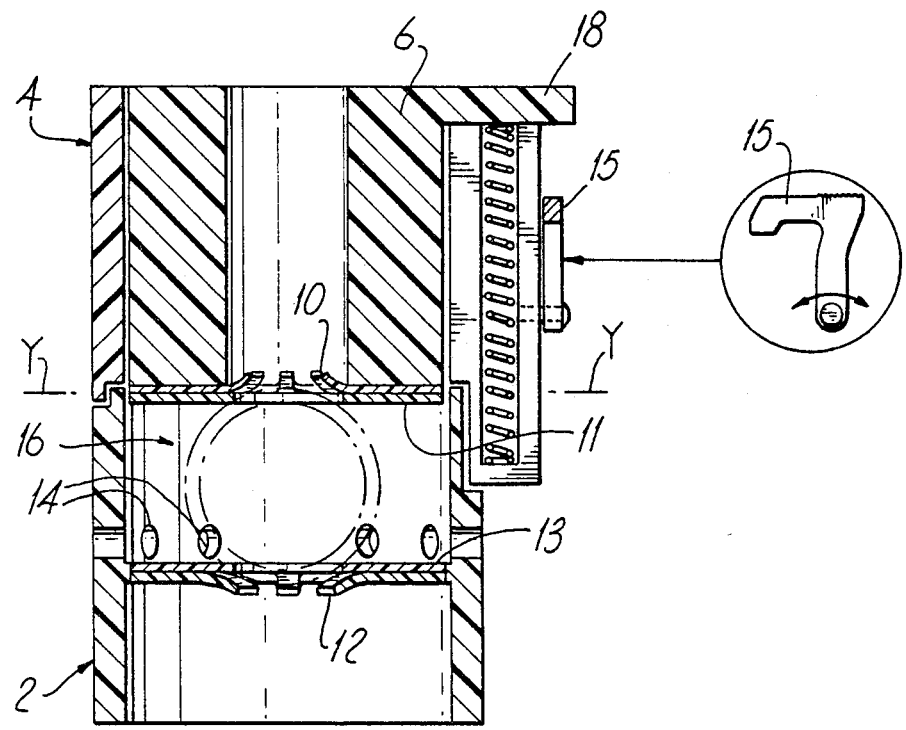
Figure 6:
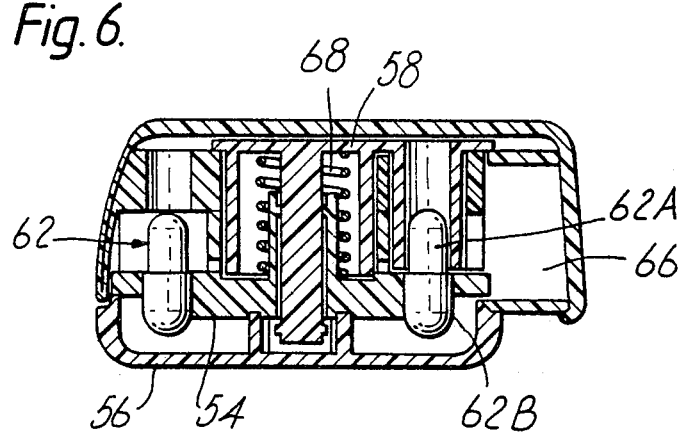
Figure 7:
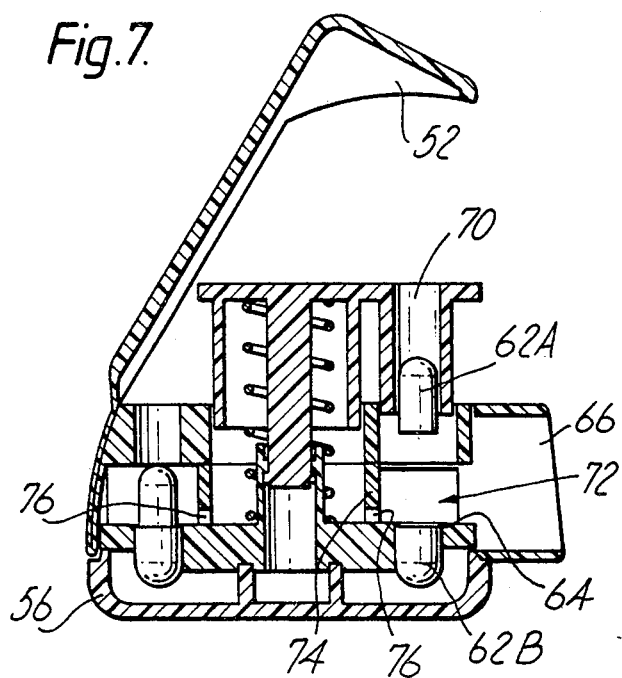
Figure 8:
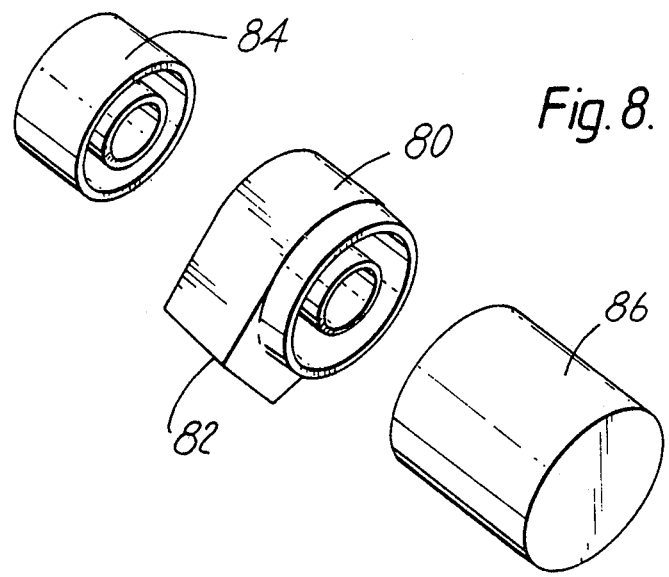
Figure 9:
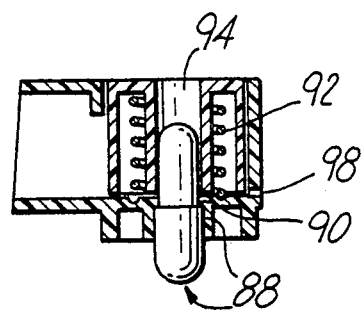
Figure 10:
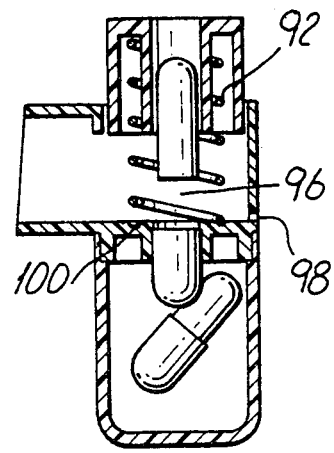
Figure 11:
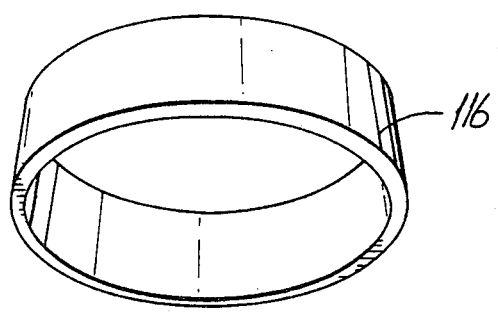
Figure 11:
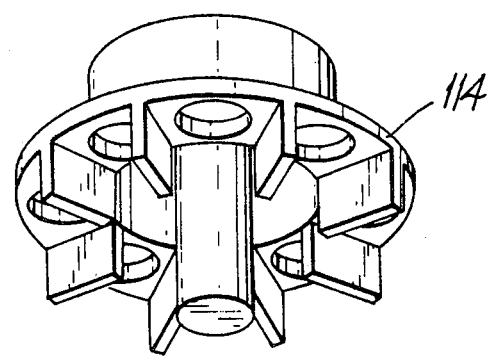
Figure 11:
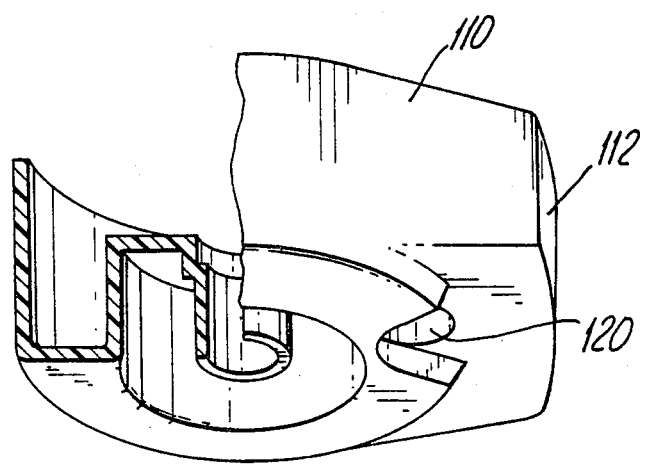
Figure 12:
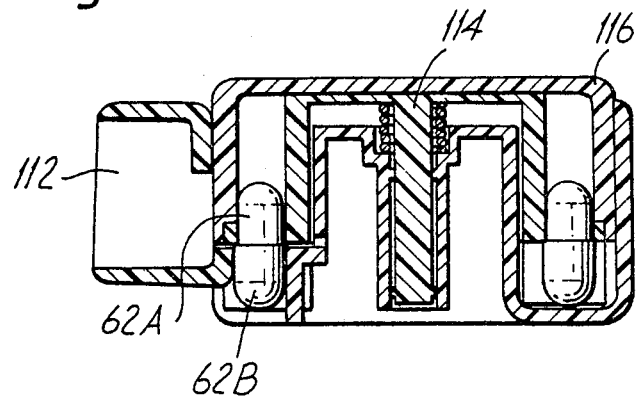
Figure 13:
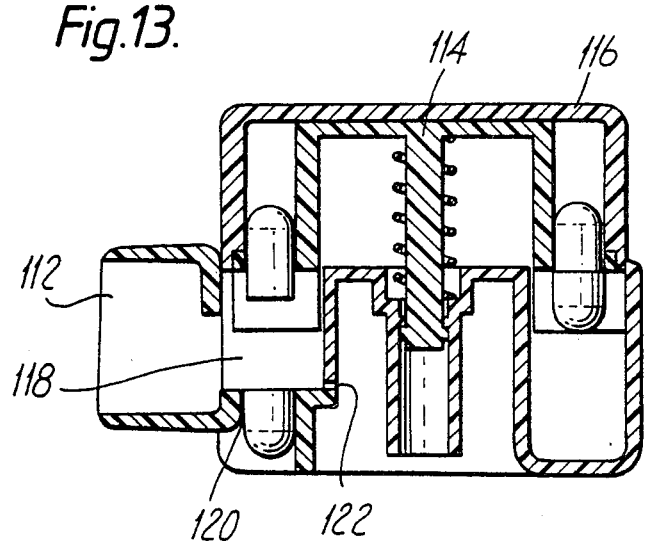
Figure 14:
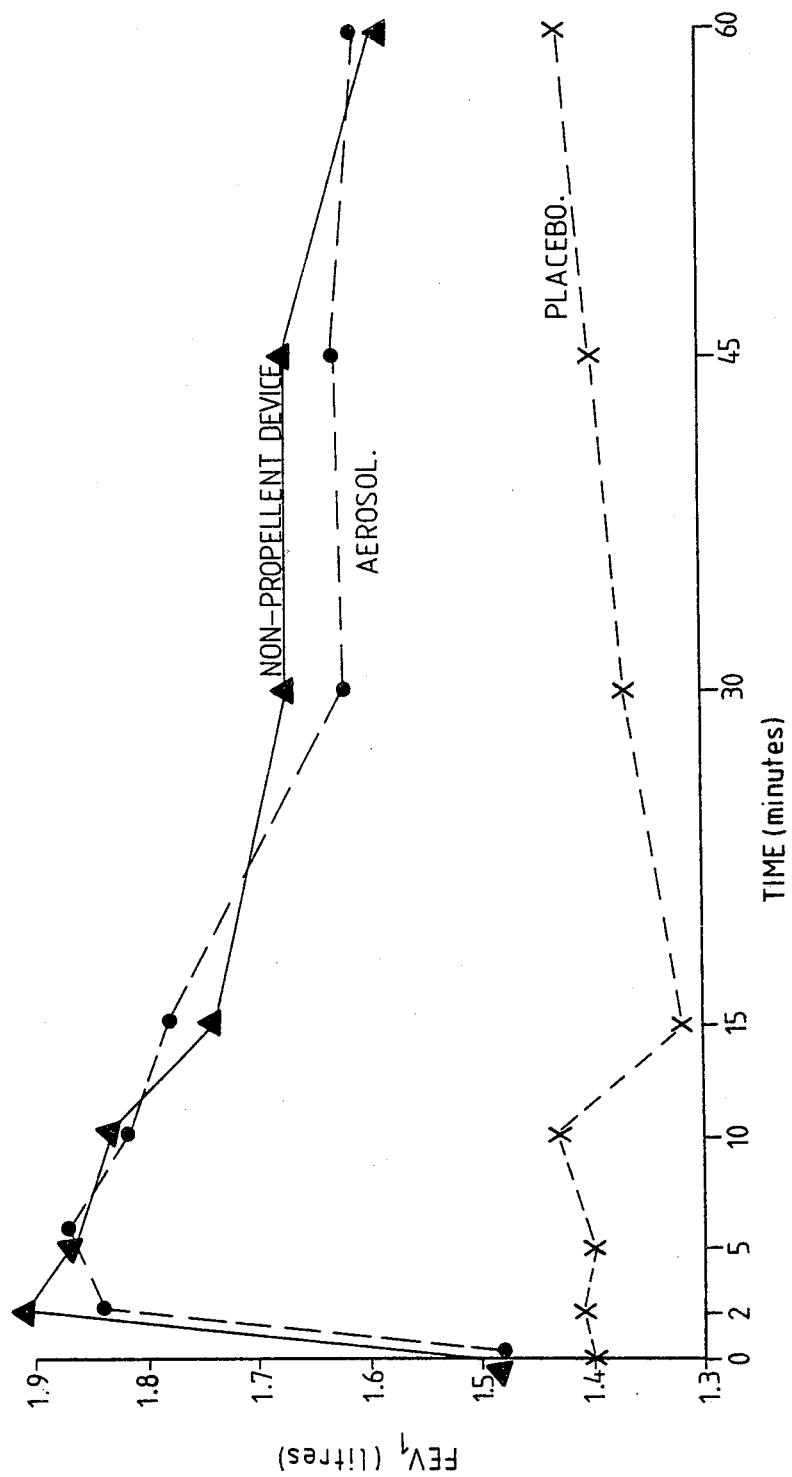

The invention will now be described with reference to the accompanying drawings, in which:

FIG. 1 represents a longitudinal section through a device in accordance with the invention, FIG. 2 is a cross-section along the line X—X of FIG. 1, FIG. 3 is a diagram showing the construction of a conventional capsule for powdered medicament, FIGS. 4 and 4a are longitudinal sections through modified versions of the device shown in FIG. 1, FIGS. 5 to 7 show a further device in accordance with the invention, the views being respectively an exploded view, a section with lid closed and a section in use, FIGS. 8 to 10 show a further device in accordance with the invention, the views being respectively an exploded view, a section during the loading operation and a section in use, FIGS. 11 to 13 show a plan view and sections with the lid open and closed respectively of a further device in accordance with the invention, and FIG. 14 is a plot of ($FEV_1$) against time summarising results of a clinical trial reported hereinafter.

The inhalation device shown in FIGS. 1 and 2 comprises a cylindrical chamber defined by two cylindrical members 2 and 4 which are joined by means of a hinge at Y—Y. Within the cylindrical chamber are two pistons 6 and 8, the lower piston 8 being free to move between two extreme positions designated in FIG. 1 by the lower position A and the higher position B shown in dashed outline. The limit of upward movement of the piston 8 is governed by an annular rim 9 which abuts the lower end of the casing of the cylindrical chamber 2.

The upper piston 6 may be lowered to touch the lower piston 8 when in position B by depressing lever 18 which acts against spring 20 positioned within housing 22. The spring 20 may be replaced by a concentric spring on the outside of the piston 6 or a plurality of springs disposed about the circumference of the piston 6 in a similar manner to spring 20. The parallel end surfaces of the pistons 6 and 8 house clutch mechanisms 10 and 12 for gripping the lid and base components of the capsule. The clutch mechanism in each piston is positioned behind a flat concentric disc 11 and 13 respectively and consists of an annulus of any thin springy material such as copper-beryllium foil or plastics, e.g. polypropylene. A number of radial slots are provided in the inner circumference of the annulus to form a ring of small flexible teeth which can grip the capsule and effectively prohibit its movement back into the chamber.

The apertures and clutch arrangements in the discs 11 and 13 may conveniently be dimensioned to accommodate conventional capsules used in the pharmaceutical industry as illustrated in FIG. 3. Such capsules comprise a body 30 which is a force fit within a cap 32. Such capsules may be used either way up in the devices of the invention, i.e. the cap 32 may constitute the lid or the base portion of the capsule. Preferably the powdered material is retained in the cap 32 and the body 30 removed since the position of the cap with respect to the airflow is not as critical as when the body 32 is used. In the device depicted in FIG. 1 the aperture in the disc 11 is large enough to accept the body 30 of the capsule but not the cap 32 and the aperture in the disc 13 is large enough to accept the cap 32.

The cylindrical chamber is provided with six air inlet ports 14 which are coplanar at X—X and consist of radial apertures disposed over an arc up to 180°. The diameter of the air inlet ports may be 2 mm. A cylindrical mouthpiece 16 is provided diametrically opposite the inlet ports such that the axis of the mouthpiece bisects the angular spread of the inlet ports when viewed from above (the axes being in different planes). The lower extent of the inlet ports is higher than the lower extent of the mouthpiece but lower than the axis of the mouthpiece. When the lower piston 8 is in position B its top surface, the top of the capsule base component, and the lower extent of the inlet ports are coplanar. With this arrangement of inlet ports, the pressure drop developed across the device during normal inhalation may be kept sufficiently low as to be almost unnoticeable to the patients. For example, for a pulmonary inhalation rate of 28.3 l/min the pressure drop developed may be equivalent to a 4.7 cm head of water. The arrangement of the inlet ports and mouthpiece may be selected to obtain the desired pressure drop which is generally maintained below 25 cm of water at an inhalation rate of 28.3 l/min.

The device is operated as follows.

The device is opened by pivoting about the hinge at Y—Y. A capsule having a body 30 and a cap 32 is inserted body first through the aperture in the surface 11 and is gripped by the clutch mechanism 10. The capsule is pushed in until the cap of the capsule abuts the surface of the disc 11. In this position the complete cap protrudes from the disc 11.

The device is then closed and with the lower piston 8 held in position B, the upper piston 6 is lowered by depressing lever 18. The cap is pushed into the aperture of disc 13 and is gripped by clutch 12. The upper piston 6 is then allowed to return to its original position under the action of the spring 20. This action pulls the two halves of the capsule apart with the powdered medicament located in the cap which is held vertically in the clutch 12. The lower piston 8 is allowed to fall to its rest position at A.

The patient inhales through the mouthpiece 16, the piston 8 is accelerated upwards to position B, air flows through the inlet ports directly across the open end of the cap and powder flows out of the cap becoming entrained in the air flow and thus passes through the mouthpiece and into the alveolar region of the lungs of the patient. The empty halves of the capsule are subsequently ejected from the clutch mechanisms of the device upon insertion of a new capsule.

The efficiency of the device in transferring powdered medicaments into the alveolar region of the lungs may be determined by measuring the particle size distribution of a micronized bronchodilating drug emitted from the device on an aerodynamic particle sampler known as the Andersen sampler Model No. 22-000 manufactured by Andersen 2000 Inc. of Atlanta, Ga., United States of America, which is a recognised instrument for measuring airborne particle size distributions. In particular the amount of drug collected on stages 3 to 7 of the Andersen sampler which represents particles between 4.7 μm and 0.43 μm, was observed. This fraction represents the amount of drug which is small enough to be transmitted into the lungs and is known as the respirable fraction.

In one series of tests 15 mg samples of a blend of micronised isoprenaline sulphate (100 μg) in powdered lactose was introduced into standard size 4 capsules. See Remingtons Pharmaceutical Sciences, Mack Publishing Company, 15th Edition, 1975 pages 1598 to 9 for details of capsule sizes. A capsule was inserted cap downwards in a device of the invention. The device was connected to the Andersen sampler and air was drawn through the system at a rate of 28.3 l/min. The resultant respirable fraction calculated as a percentage of the total dose of drug originally packed in the capsule obtained with the new device is given below together with respirable fractions obtained on the Andersen sampler with two other prior art devices using the same powder formulations:

| Device | Respirable Fraction |
|---|---|
| Device of the invention | 20.3% |
| British Patent No. 1 182 779 | 9.1% |
| U.S. Pat. No. 4 117 844 | 3.9% |

These results confirm the efficiency of the device of FIG. 1 of the invention over devices of the prior art.

It has been found that when capsules are used in which the powder is uncompacted and free flowing the efficiency of drug transfer into the lungs is substantially the same for the following situations:

(i) when the sliding piston 8 is allowed to slide during inhalation from position A to position B, and (ii) when the piston is held static in position B.

However, when highly cohesive or compacted powders are present in the capsules the sliding piston arrangement (i) is considerably more efficient that the static arrangement (ii) as shown in the following table:

| | Sliding Piston | Piston held static in position B |
|---|---|---|
| Average removed as % of total | 78% | 44% |

A further series of tests was performed to examine the efficiency of the airflow directly across the open capsule portion in the device of the invention compared with an airflow deflected into the capsule portion.

A deflector to channel the inspired air into the capsule containing the drug blend was built into a device of the invention with the clutch holder static in position B. A determination was made by an Andersen Sampler of the respirable fraction obtained by using this modified device with a blend of micronised rimiterol hydrobromide 0.25 mg with lactose 45 mg. The respirable fraction obtained from the same blend using a similar device without a deflector was also determined. The results are shown in the following table.

| Drug found as % of total drug filled into capsules | No Deflector | | Deflector | |
|---|---|---|---|---|
| | 1 | 2 | 1 | 2 |
| Capsules and device | 12.4 | 11.1 | 13.1 | 15.7 |
| Throat and pharynx of Andersen | 53.7 | 57.6 | 52.1 | 55.0 |
| Upper Andersen | 17.8 | 16.5 | 18.4 | 14.6 |
| Andersen plates 3 to 7 (respirable fraction) | 16.1 | 14.8 | 16.3 | 14.7 |

The results indicate that inclusion of a deflector did not increase the respirable fraction.

Detailed tests were undertaken to compare the efficiency of a device of the invention with that illustrated in FIGS. 4 and 5 of U.S. Patent Specification No. 4 210 140.

In the device of the prior art an opened capsule has its long axis horizontal and parallel to the mouthpiece. The unopened capsule is fitted into clutch mechanisms one of which is movable to pull the capsule apart. In practice difficulty was experienced in separating the capsule halves.

The respirable fraction was determined upon size 4 capsules containing a blend of micronised rimiterol hydrobromide 0.25 mg and lactose 45 mg as in the preceding tests. Four determinations were performed according to the position of the powder:

A. divided approximately equally between the two capsule halves,

B. all in the capsule half with its open end facing away from the mouthpiece,

C. all in the capsule half with its open end facing the mouthpiece, and

D. deliberately tipped onto the floor of the chamber.

The results are shown in the following table.

| Locus of Drug (% of total drug filled into capsules) | A | B | C | D |
|---|---|---|---|---|
| Capsule and device | 91.6 | 92.3 | 91.7 | 23.2 |
| Throat and pharynx | 3.2 | 3.3 | 2.5 | 51.8 |
| Upper Andersen | 2.9 | 2.4 | 2.9 | 16.7 |
| Respirable fraction | 2.4 | 1.9 | 2.9 | 8.4 |

The device is very inefficient from the point of view of pulling apart the capsule and the airflow leaves 90% of the powder blend in the capsule unless the powder is deliberately tipped onto the floor of the chamber. This results in a very low respirable fraction (<3%). The respirable fraction is low (8%) even when the powder is spilt deliberately out of the capsule before inhalation commences.

The bronchodilator effect of 200 μg isoprenaline sulphate as delivered to a sample of 12 patients by the non-propellant device of the invention and by a pressurized aerosol commercially available from Riker Laboratories under the trade mark Medihaler, was compared together with a control in which a placebo preparation was administered by both devices. The bronchodilator effect was compared by measuring the forced expiratory volume in one second ($FEV_1$) for patients before and after administration of the drug and the average results are recorded in FIG. 11 as a plot of $FEV_1$ against time.

There was no statistically significant difference between the values of the measured pulmonary function parameters resulting from the application of the drug by each device. However, both modes of application of the drug produced a significant change in pulmonary function compared with a placebo administered by both modes of delivery.

In the embodiment shown in FIG. 4, the device is identical to that shown in FIG. 1 with the exception that the cylindrical member 2 is elongated to form a skirt portion 40 which completely surrounds the lower piston 8 when in its lower position A thereby protecting the piston from damage and preventing the user's fingers from interfering with its free movement. The skirt portion 40 includes a vertical slot 42 through which arm 44 attached to the piston 8 protrudes thus enabling the piston to be raised and held at its upper position B when required for opening the capsule.

In a second modification of the device of FIG. 1 illustrated in FIG. 4a the bottom sliding piston is replaced by a fixed base 13 housing a clutch mechanism 12 at a position corresponding to the higher position B of the sliding piston (FIG. 1). This modification makes the device simpler and more compact. In addition, by incorporating a locking mechanism 15 into the device which will enable the piston 6 to be locked securely at its lowest extent of travel with its end surface touching the fixed base, the device may be pre-loaded with a capsule which will be firmly held at all times by the two clutch mechanisms. When medication is then required the user need only unlock the piston and return it to its upper position thus opening the pre-loaded capsule. The piston need not be spring-loaded but may instead be secured at both the lower and higher positions. Pre-loading the device in this manner reduces to a minimum the effort required by the user at a vital time when relief from, for example, an asthmatic attack is being sought.

Figure 5:
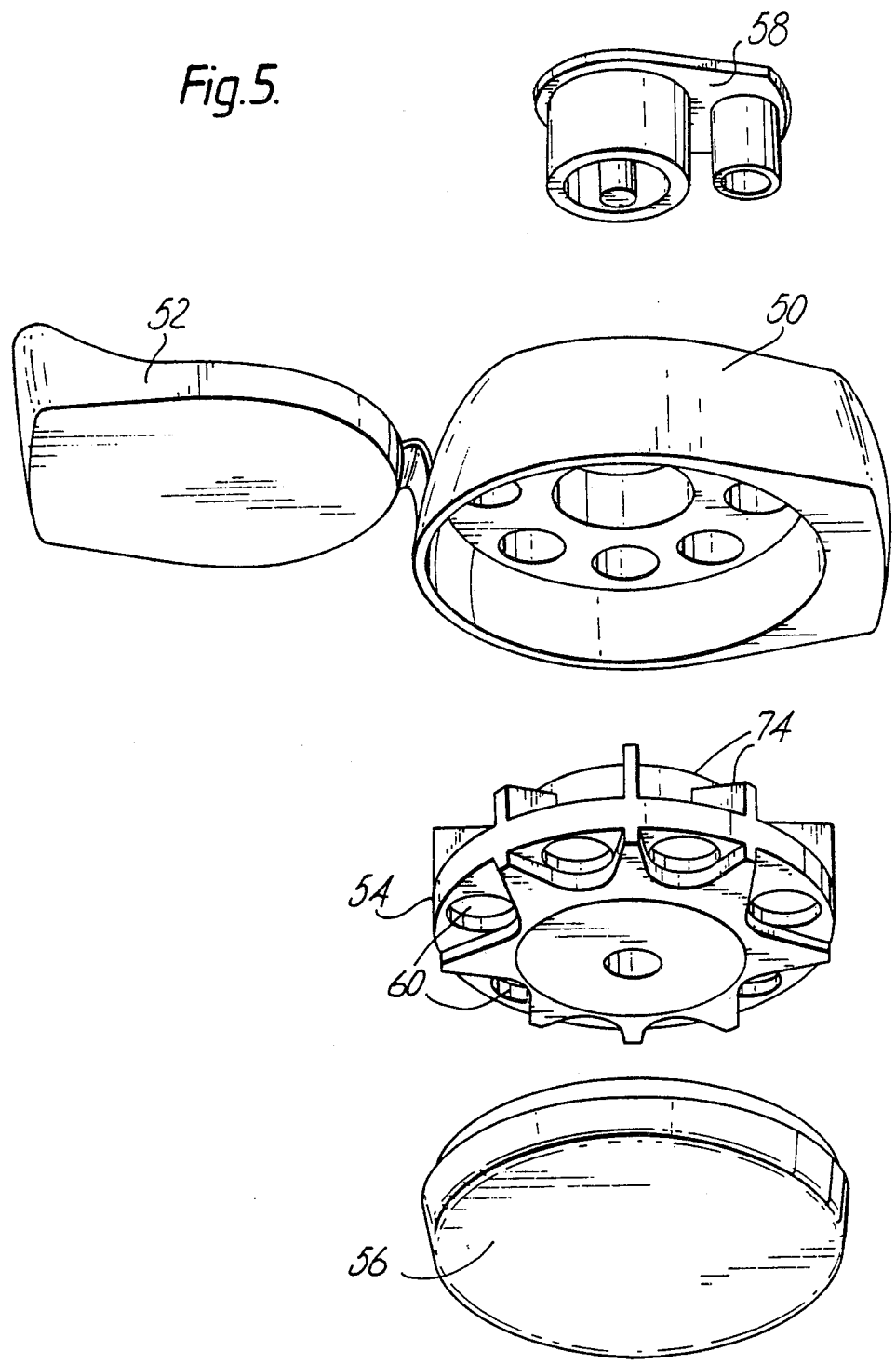

FIGS. 5 to 7 show a preferred embodiment of the invention in which the device contains a plurality of capsules which may be used sequentially. The device comprises a body portion 50 having a hinged lid 52, a rotatable carousel 54, a base cap 56 and a movable piston assembly 58. The carousel 54 is formed with a number of apertures 60 adapted to support capsules 62. The capsules 62 comprise a lid component 62A which is a force fit within a base component 62B. The apertures 60 in the carousel have a lip 64 against which the edge of the base component 62B abuts to prevent the base component of the capsule passing completely through the aperture.

The body of the device includes a short mouthpiece 66 which is covered by the lid 52 when the lid is closed. The piston assembly 58 is movable between the two positions shown in FIGS. 6 and 7, the assembly being biased by spring 68 so that upon opening of the lid it adopts its raised position as shown in FIG. 7. The piston assembly includes an aperture 70 of a suitable size to accommodate the lid component 62A of a capsule 62. The apertures 60 in the carousel and aperture 70 in the piston assembly may include a suitable clutch means as illustrated in FIGS. 1 to 4.

The chamber 72 of the device is defined by various portions of the carousel, body and piston assembly. In particular, moulded portions 74 on the carousel define the side walls, these mouldings being provided with apertures 76 forming the air inlet ports. The inlet ports are positioned so that in use air flows through the inlet ports directly over the base component 62B of the capsule and out through the mouthpiece 66.

The capsule is opened in the chamber by depressing piston assembly 58 so that the aperture 70 accommodates the lid component of the capsule 62A. Upon releasing the piston assembly it is urged to its raised position as shown in FIG. 7 taking the lid component of the capsule 62A with it, thereby opening the capsule as shown in FIG. 7. The device is then ready for inhalation.

The device may readily be arranged such that upon opening the lid 52 a capsule in the chamber is automatically opened and the device ready for immediate use. After use the rotatable carousel may be advanced so that a new capsule is positioned in the chamber so that when the device is closed the piston assembly will engage the lid component of the new capsule ready for opening when the lid 52 of the device is opened. Automatic advancement of the carousel may be effected by a suitable ratchet mechanism, which may be operated, for example, by closing the lid.

FIGS. 8 to 10 show an alternative device which must be recharged manually after use. The device comprises a body portion 80 incorporating a mouthpiece 82, a piston assembly 84 and a capsule holder 86. A capsule 62 is manually inserted in an aperture 88 in the body portion as shown in FIG. 9. The aperture 88 has a lip portion 90 equivalent to the lip 64 in FIGS. 5 to 7. The piston assembly 84 is movable between a lower and upper position as shown in FIGS. 9 and 10 respectively, the piston being spring biased by a spring 92. The piston assembly includes an aperture 94 for accommodating the lid component of the capsule 62A in a similar manner to aperture 70 in FIGS. 5 to 7.

The chamber 96 of the device is defined by the body portion and piston assembly and includes apertures 98 which are arranged so that in use the airflow is directly across the base component of the capsule 62B. The mode of operation of the piston assembly is similar to that shown in FIGS. 5 to 7 although the piston is depressed manually. The foot of the spring 92 is arranged in an annular depression 100 in the base of the chamber so that there is no disruption of the airflow over the base component of the capsule 62B, the pitch of the spring being sufficiently large so that the coils of the spring do not obstruct the airflow.

The capsule holder 86 may contain a plurality of capsules and is removed from the body portion when a new capsule is to be inserted.

FIGS. 11 to 13 show a further device according to the invention which comprises a body portion 110 (shown in part section in FIG. 11) incorporating a mouthpiece 112, a carousel 114 and a cover 116. In this device the rotatable carousel 114 also forms the piston assembly and the capsules 62 are loaded by inserting their lid component 62A into the apertures of the carousel. The arrangement of the carousel is similar to that shown in FIGS. 5 to 7 and includes moulded portions to define parts of the side wall of the chamber.

The body portion is moulded to define a substantial portion of the chamber 118 and includes an aperture 120 adapted to accommodate and retain the base component of a capsule 62B. Apertures 122 form the air inlet ports which are arranged so that in use an airflow is established directly across the base component of the capsule. The capsule is opened in the chamber by depressing the cover 116 and hence the carousel 114 so that the base component of the capsule held in the carousel engages in an aperture 120. Upon releasing the cover the carousel and cover is spring biased to the raised position shown in FIG. 13 thereby removing the lid component of the capsule 62B from the base component of the capsule 62A. The device is then ready for use. After use the carousel is advanced to position the next capsule within the chamber. The spent base component of the capsule 62B is pushed through the aperture 120 when a new capsule is inserted.

Whilst the arrangement shown in FIGS. 11 to 13 requires the carousel to be rotated manually, the device may be constructed so that the carousel is advanced automatically, for example by a ratchet mechanism, as the lid is depressed to facilitate ease of operation of the device.

We claim:

1. A breath actuated device for the oral inhalation by a person of medicaments in finely divided powder form from within a capsule comprising a base component having a cavity containing the powder and a rim defining an outlet aperture communicating with the cavity, and a lid component releasably engaging said base component over said outlet aperture, said device comprising:

wall members defining a chamber, having at least one inlet port for the entry of air into said chamber, and a mouthpiece having a through outlet in direct communication with said chamber, said inlet port, mouthpiece and outlet opening being aligned to provide airflow in a single generally horizontal plane through said inlet port chamber and outlet when the device is positioned normally for operation by inhalation of the person through the mouthpiece;

means positioned adjacent the chamber for supporting the base component of a said capsule containing the powder within the chamber with the rim of the base component uppermost, generally horizontal, and in the plane of the airflow through said inlet port, chamber, and outlet when the device is positioned normally for operation by inhalation of the person through the mouthpiece, and means adapted for manual activation for removing the lid component of a said capsule having its base component in said means for supporting.

2. A device according to claim 1, in which said means for supporting is adapted to support a said base component with its rim substantially aligned with or lower then the lower extent of said inlet port when the device is positioned normally for operation by inhalation of the person through the mouthpiece.

3. A device according to claim 1 in which the lower extent of the inlet port is higher than the lower extent of the outlet when the device is positioned normally for operation by inhalation of the person through the mouthpiece.

4. A device according to claim 1 in which the vertical extent of the inlet ports is wholly within the vertical extent of the outlet when the device is positioned normally for operation by inhalation of the person through the mouthpiece.

5. A device according to claim 1 wherein said wall members defining said chamber form a body member defining said mouthpiece and side walls for said chamber in which said inlet port is formed, and a first piston member defining an upper wall of said chamber when the device is positioned normally for operation by inhalation of the person through the mouthpiece, said first piston member includes means for engaging the lid component of a said capsule and is manually moveable relative to said body member between an engaging position at which said means for engaging engages the lid component of the capsule held by its base component in said means for supporting, and a dispensing position further spaced from said means for supporting to provide said means for removing in that movement of said first piston member from its engaging position to its dispensing position causes separation of the lid component from the base component of the capsule.

6. A device according to claim 5 further including spring means for biasing said first piston member to its dispensing position.

7. A device according to claim 5 wherein said wall members further form a second piston member defining the base of the chamber when the device is positioned normally for operation by inhalation of the person through the mouthpiece, which second piston member includes said means for supporting the base component of a said capsule, said second piston member being moveable relative to said body member between a first position defined by engagement of said second piston member with a stop on said body member with the rim of the base component of a said capsule in said means for supporting in said plane of airflow, and a second position with the rim and base component spaced from said plane of airflow, and means for moving said second piston member from its second to its first position when the device is operated by inhalation of a person through said mouthpiece to give impetus to powdered medicament contained in the base component of the capsule.

8. A device according to claim 5 wherein said means for engaging the lid component comprises a ring of radially inwardly projecting teeth on said piston member.

9. A device according to claim 5 wherein means for supporting the base component of a said capsule comprises a carousal defined by said wall members and including means for supporting a plurality of said capsules, said carousal being rotatably mounted on said body member so that each capsule in turn may be positioned within said chamber, opened by manual operation of said piston member and the medicament entrained in air flow in said plane upon inhalation of the person through said mouthpiece.

10. A device according to claim 9 wherein the base component of each of said plurality of capsules is integrally formed in said carousal.

11. A device according to claim 9 wherein said carousal forms at least a portion of a bottom wall of the chamber around the capsule in said means for supporting.

12. A device according to claim 9 wherein said wall members further define a lid hinged to said body member, which cover when closed covers the carousal, first piston member and mouthpiece.

13. A device according to claim 12 wherein closing of said lid moves said first piston to said engaging position and opening of said lid affords movement of said first piston member to said dispense position.

* * * * *